United States Patent [19]
Danforth

[11] Patent Number: 5,211,667
[45] Date of Patent: May 18, 1993

[54] GUARD FOR RESIDUUM AFTER AMPUTATION

[76] Inventor: Michael B. Danforth, 55 Interlaken Rd., Orlando, Fla. 32804

[21] Appl. No.: 872,131

[22] Filed: Apr. 22, 1992

[51] Int. Cl.$^5$ .......................... A61F 2/80; A61F 2/78; A61F 2/60
[52] U.S. Cl. ...................................... 623/35; 623/36; 623/33
[58] Field of Search .................................. 623/33–37, 623/57

[56] References Cited

U.S. PATENT DOCUMENTS

| | | | |
|---|---|---|---|
| 4,842,608 | 6/1989 | Marx et al. | 623/33 |
| 4,923,474 | 5/1990 | Klasson et al. | 623/33 |

FOREIGN PATENT DOCUMENTS

| | | | |
|---|---|---|---|
| 0675386 | 2/1966 | Belgium | 623/36 |
| 2729800 | 1/1979 | Fed. Rep. of Germany | 623/34 |
| 2830988 | 1/1980 | Fed. Rep. of Germany | 623/36 |
| 0305888 | 6/1971 | U.S.S.R. | 623/36 |

Primary Examiner—Randall L. Green
Assistant Examiner—D. Willse
Attorney, Agent, or Firm—Macdonald J. Wiggins

[57] ABSTRACT

A prosthesis for guarding a residual limb after a lower limb amputation includes an upper shell, lined with a soft material, and matching the limb residuum. A lower shell telescopes over the upper shell. Each shell has a slot in its lower end. A first high density foam pad is disposed in the lower shell such that the lower end of the upper shell rests thereon. The patient dons a stump sock having an elongate thin strap at its distal end. The strap is threaded through a second soft plastic foam pad, the slot in the lower end of the upper shell, the high density foam pad in the lower shell, and through the slot in the lower end of the second shell. Fasteners are provided for anchoring the strap to an external surface of the lower shell. The shock due to a patient falling on the residuum is absorbed by the lower shell telescoping further over the upper shell to permit the pads to compress, as well as by the compression of air between the shells.

11 Claims, 1 Drawing Sheet

U.S. Patent
May 18, 1993
5,211,667
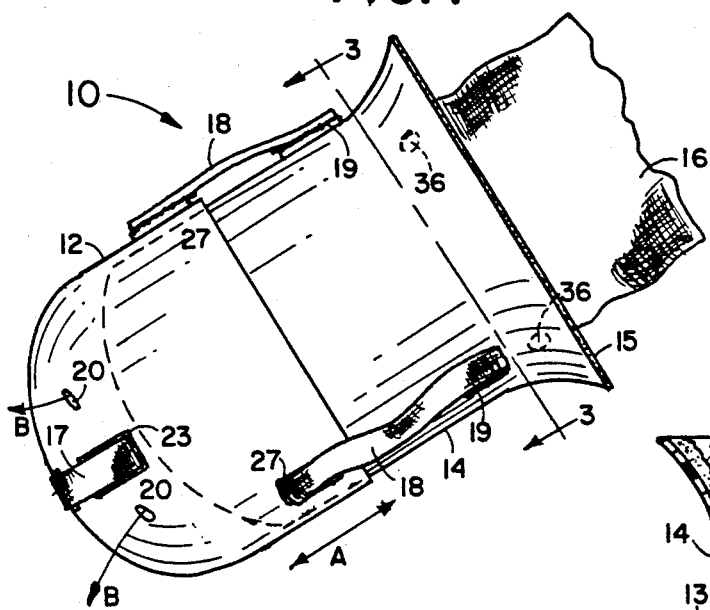
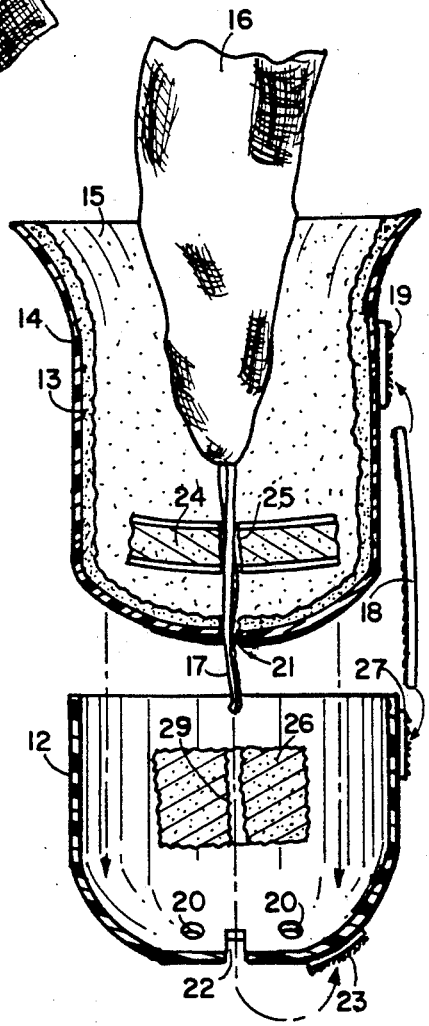
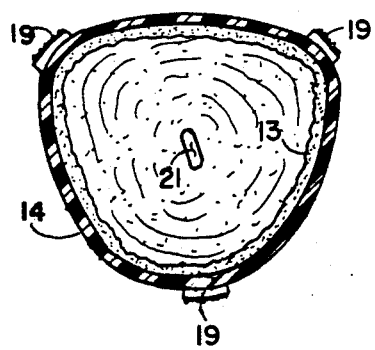
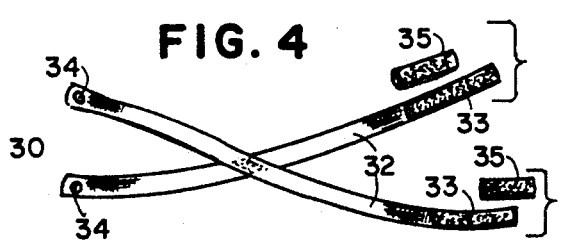

GUARD FOR RESIDUUM AFTER AMPUTATION

BACKGROUND OF THE INVENTION

1. Field of the Invention

The present invention relates to lower limb prosthetics, and more particularly to a guard for a residuum after an amputation of a lower limb.

2. Description of the Prior Art

After amputation of a lower limb, the residuum, or stump, will begin to shrink for a period of time. Thus, a prosthesis, such as an artificial limb, cannot be provided until such shrinking is essentially complete. During the period of time that the patient must wait, it is necessary to protect the residuum from injury due to falls, or similar mishaps. For example, the patient may experience "phantom" feelings as if the limb were still present, and, out of force of habit, attempt to use the missing foot resulting in a fall.

A known prior art residuum guard is disclosed in U.S. Pat. No. 721,239 to Rowley. This patent discloses a leather cuff having lacings that are periodically tightened during the shrinking phase of healing of the stump, prior to fitting of an artificial leg. Other U.S. patents related to various aspects of lower limb prosthetics are known. U.S. Pat. No. 1,319,637 discloses a combined stocking and pad for the residuum. A stump-shrinking apparatus is taught by Cremona-Bonato using a waist band and elastic straps. Marx et al. show a three-piece below knee prosthetic socket provides an adjustable volume during stump shrinkage in U.S. Pat. No. 4,842,608. U.S. Pat. No. 4,872,879 to Shank discloses a standardized prosthetic socket which can be provided in a minimal number of sizes.

SUMMARY OF THE INVENTION

The present invention is a prophylactic prosthesis for guarding a residual limb after amputation. An upper shell is molded of an extruded semi-rigid plastic to match the stump to be protected. The upper shell has an approximate hemispherical distal end. The upper shell is lined with a soft lining, for example, low density foam. A pad of thick, convoluted foam is disposed in the interior of the upper shell at the distal end of the shell. The lower half of the shell has a constant cross section.

A lower shell is extruded of semi-rigid plastic having an interior contour matching the external counter of the lower half of the upper shell. The distal end of the lower shell is essentially hemispherical, and a thick pad of high density polyethylene foam is disposed in the lower shell. Several small vent holes are formed through the hemispherical portion of the lower shell.

As will now be recognized, the lower shell will form a sliding fit over the lower end of the upper shell, resulting in a compression of air therebetween. The vent holes will permit such compressed air to escape. The shells are maintained in the initial telescoped condition during use by Velcro ® pads on each shell, and mating Velcro ® strips.

A stump soft sock has a short length of Velcro ® strip attached to the toe end. The strip is passed through a slot in the first foam pad, through a matching slot in the lower end of the upper shell, through the foam pad in the lower shell and out a slot in the lower end of the lower shell. A pad of matching Velcro ® attached to the outer surface of the lower shell receives the strip to maintain the assembly of upper and lower shells. The patient dons the guard by stretching the stump sock over the open top end of the upper shell, inserting the stump and pulling up the sock. Alternatively, an elastic stump shrinker may be utilized instead of the stump sock.

With the residuum guard in place, a fall on the prosthesis will cause the lower shell to move upward on the upper shell, compressing both foam pads, and the air in between the shells. The cushioning effect of this action protects the stump from injury. The prosthesis of the invention is installed on the residuum after surgical removal of the limb, and serves to protect the residuum from accidental injury during initial shrinkage thereof. As the residuum shrinks and the prosthetic becomes loose, new shells are prepared and installed. When the shrinkage process is completed, the limb can be fitted with a suitable artificial limb. It is a principal object of the invention to provide a residuum guard for a recent lower limb amputation that will protect the residuum from injury during an initial shrinking thereof.

It is another object of the invention to provide a residuum guard having two telescoping shells, each having compressible pads, and the lower shell slidable on the upper shell.

It is yet another object of the invention to provide a residuum guard in which the telescoping shells compress air therebetween for providing additional cushioning.

It is another object of the invention to provide a residuum guard that facilitates the patient's donning of the stump sock or shrinker.

These and other objects and advantages of the invention will become apparent from the following detailed description thereof.

BRIEF DESCRIPTION OF THE DRAWINGS

FIG. 1 is a side view of the residuum guard of the invention;

FIG. 2 is a cross-sectional and exploded view of the residuum guard;

FIG. 3 is a cross-sectional view of the guard of FIG. 1 through the plane 3—3; and FIG. 4 shows a harness for use with the residuum guard for a below the knee amputation.

DETAILED DESCRIPTION OF THE PREFERRED EMBODIMENT

Referring to FIG. 1, a side view of the residuum guard 10 is shown having an upper shell 14 having a contour formed to fit the initial contour of the limb to be protected. Interior details of the guard are shown in the cross-sectional drawing of FIG. 2.

It is desirable that the interior shape of upper shell 14 provide a comfortable fit over the patient's residuum at the time of installation. The cross sectional view of shell 14 of FIG. 3 shows a typical shape. In some instances, a mold can be made from the actual limb. However, it is possible to preform a number of standard sizes. The shell is preferably formed from a semi-rigid plastic, although other similar materials may be used. The throat of shell 14, as best seen in the FIGS. 1 and 2, is slightly flared for ease of installing on the limb. Shell 14 is lined with a low density foam 13 or similar material.

A compression pad 24 is loosely disposed within shell 14, and includes a slot 25 therethrough. Any suitable material may be used, although convoluted foam is preferred. A stump sock or shrinker sock 16 has a strip 17 of fabric having a type of hook and loop fastener, such as Velcro®, attached to the distal end thereof. Sock 16 may be formed of soft fabric in case of the stump shock, and of elastic material in the case of the stump shrinker. A slot 25 through pad 24, and a slot 21 through the lower edge of shell 14 are provided. Strip 17 is passed through slot 25 of pad 24, and through slot 21 of shell 14.

As may be noted from FIGS. 1 and 2, lower shell 12 has an interior shape that essentially matches the exterior contour of upper shell 14, and can slide freely therealong. Shell 12 includes a thick compression pad 26 having a slot 29 therethrough. Pad 26 may be formed of high density polyethylene foam, or similar material. The strip 17 is passed through slot 29 of pad 26 and through a slot 22 in the lower edge of shell 12. A pad 23 of hook and loop material complementary to the material of strip 21 is cemented to shell 12 adjacent slot 22. Strip 17 is anchored thereto, and holds guard 10 on the patients limb by virtue of stump sock 16. Pads 19 of hook and loop fastening material are cemented to shell 14 near the upper end thereof and aligned with similar pads 27 along the upper edge of shell 12. After telescoping the shells to the point that the lower edge of shell 14 bottoms on pad 26, strips 18 having hook and loop fastening material complementary to those of pads 19 and 27 are attached as shown in FIG. 1 to assist in holding shells 12 and 14 in the telescoped position.

As will be apparent, a patient having the residuum guard in position on a limb may fall directly on the lower end of the guard 10, and the lower shell 12 will move upward on shell 14, compressing pad 26, and pad 24. The major shock will be absorbed by pad 26. Additionally, air present in the space will be compressed providing additional cushioning, thus minimizing the shock to the sensitive residuum. The rate of movement is controlled by a set of bleed or vent holes 20 in the lower edge of shell 12.

To don the residuum guard 10, the guard 10 is assembled as shown in FIG. 1. The stump or shrinker sock is inserted into shell 14 and strip 17 inserted through slots 25, 21, and 26. Strip 17 is then inserted through slot 22. Lower shell 12 is telescoped over upper shell 14 until the lower end of shell 14 bottoms on pad 26 without compressing this pad as strip 17 is pulled through slot 22. Strip 17 is then anchored to fastener pad 23 on the outer surface of lower shell 12. Next, the proximal end of sock 16 is rolled down over the flared edge 15 such that the distal end is partially stretched across shell 14. The stump is then inserted into the sock 16 and shell 14, and the sock rolled up the limb residuum. Shell coupling strips 18 are installed between hook-loop pads 19 and 27 to maintain lower shell 12 in place over upper shell 12. As will now be recognized, shell 12 can move upperward when upward pressure is placed on the lower end of shell 12, and extend when such pressure is removed as indicated by arrow A of FIG. 1. Pads 24 and 26, as well as air between shells 14 and 12 serve to slow the rate of movement, and thereby absorb shock.

FIG. 4 shows a harness 30 having a pair of crossed straps 32 for use with the residuum guard 10 to protect a below-the-knee residuum. Upper shell 14 will have optional fastener holes 36 (FIG. 1) for this application, and straps 32 may be attached thereto by riveting or the like. A set of fastener pads 35 may be attached to the rear aspect of shell 14. Straps 32 are wrapped around the patient's thigh and mating fastener pads 33 anchored to pads 35.

The invention has been disclosed with reference to the preferred embodiment. However, there may be other materials suitable for fabricating the residuum guard. Other means for holding the upper and lower shells together will be apparent to those of ordinary skill in the art. Such changes and substitutions are considered to fall within the spirit and scope of the invention.

I claim:

1. A prosthesis for protecting a residuum of a lower limb amputation from injury comprising:
    a) an upper shell formed to essentially match the contour of the residuum, said upper shell having a first closed lower end, said end including a first slot therethrough;
    b) a lining of soft material disposed over an inner surface of said upper shell;
    c) a first compressive pad disposed over an inner surface of said first closed end of said upper shell, said first pad having a second slot therethrough;
    d) a lower shell having an inner contour complementary to an external contour of said upper shell thereby permitting said lower shell to telescope over said upper shell, said lower shell having a second closed lower end, said second closed lower end having a third slot therethrough;
    e) a second compressible pad disposed over said second closed end, said second pad having a fourth slot therethrough;
    f) a post-operative stump sock having a flexible strip attached at a distal end of said sock, said strip passed through said second slot, said first slot, said third slot, and said fourth slot with said lower shell telescoped over said upper shell; and
    g) fastening means for attaching said strip to an external surface of said lower shell for maintaining said lower shell telescoped over said upper shell, whereby pressure on said lower shell causes said lower shell to further telescope over said upper shell, and to compress said first and second pads.

2. The prosthesis as defined in claim 1 in which said upper shell and said lower shell are formed of a semi-rigid plastic.

3. The prosthesis as defined in claim 1 in which said soft material is a low density foam material.

4. The prosthesis as defined in claim 1 in which said fastening means is a first hook-and-loop material attached to said sock strip, and a mating pad of said hook-and-loop material attached to an outer surface of said lower shell.

5. The prosthesis as defined in claim 1 which further comprises:
    a plurality of first hook-and-loop fastening material pads attached to an external surface of said upper shell;
    a plurality of second hook-and-loop fastening material pads attached to an external surface of said lower shell; and
    a plurality of elongate shell fastening strips, each having a pad of hook-and-loop fastening material, mating with said first and second fastening material pads, attached to each end thereof, said fastening strips attached between said first and second fastening material pads to maintain said upper and lower shells in a telescoped relationship.

6. The prosthesis as defined in claim 1 in which said first compressive pad is formed of convoluted foam material.

7. The prosthesis as defined in claim 1 in which said second compressible pad is formed of a high density polyethylene foam material.

8. The prosthesis as defined in claim 1 in which said lower shell includes at least one air bleed hole through a lower end thereof.

9. The prosthesis as defined in claim 1 in which said upper shell has an open mouth portion for accepting the residuum, said mouth portion flared outwardly.

10. The prosthesis as defined in claim 1 which further comprises a harness attached to said upper shell for installing said prosthesis on a below-the-knee residuum.

11. A temporary post-surgical prosthesis for protection of a residuum of a lower limb during shrinkage thereof comprising:

a) a hollow first shell having a contour of an upper portion thereof molded to match a contour of the residuum, said upper portion having essentially straight external surfaces, and a closed curved lower end, said closed end having a first slot in a central portion thereof;

b) an inner lining of said first shell, said lining formed of a soft, slightly compressible material, formed to fit the residuum;

c) a hollow second shell having an upper inner contour complementary to an external contour of said first shell, and an essentially hemispherically shaped closed lower end, said second shell lower end having a second slot therethrough, said second shell telescoped over the external surface of said first shell and movable therealong;

d) a first compressive pad disposed between said external lower end of said first shell and an internal surface of said second shell, said first pad having a third slot therethrough;

e) a second compressive pad having a fourth slot therethrough and disposed within said first shell;

f) a post-operative stump sock having a flexible strip attached at a distal end thereof whereby said strip is passed through said fourth, first, third, and second slots; and g) means for securing said strip to said second shell for maintaining said second shell telescoped over said first shell.

* * * * *